US008529128B2

(12) United States Patent
Horiuchi

(10) Patent No.: US 8,529,128 B2
(45) Date of Patent: Sep. 10, 2013

(54) RADIATION IMAGING APPARATUS WITH ASSISTED MOVEMENT

(75) Inventor: Hisatsugu Horiuchi, Kanagawa-ken (JP)

(73) Assignee: FUJIFILM Corporation, Tokyo (JP)

( * ) Notice: Subject to any disclaimer, the term of this patent is extended or adjusted under 35 U.S.C. 154(b) by 532 days.

(21) Appl. No.: 12/659,105

(22) Filed: Feb. 25, 2010

(65) Prior Publication Data

US 2010/0213383 A1   Aug. 26, 2010

(30) Foreign Application Priority Data

Feb. 26, 2009   (JP) .................................. 2009-043526
Aug. 24, 2009   (JP) .................................. 2009-192771

(51) Int. Cl.
  *H05G 1/02*   (2006.01)
(52) U.S. Cl.
  USPC .......................................... 378/197; 378/196
(58) Field of Classification Search
  USPC ..................................... 378/91, 196, 197, 198
  See application file for complete search history.

(56) References Cited

U.S. PATENT DOCUMENTS

| | | | | |
|---|---|---|---|---|
| 3,866,048 A * | 2/1975 | Gieschen et al. | ................ | 378/91 |
| 4,868,845 A * | 9/1989 | Koropp | ........................... | 378/204 |
| 5,050,202 A * | 9/1991 | Yanome | ........................ | 378/167 |
| 5,159,622 A * | 10/1992 | Sakaniwa et al. | ............. | 378/196 |
| 5,351,282 A * | 9/1994 | Kadowaki et al. | ............ | 378/198 |
| 6,045,262 A * | 4/2000 | Igeta et al. | ..................... | 378/209 |
| 6,409,382 B1 * | 6/2002 | Akutsu et al. | ................. | 378/198 |
| 6,412,978 B1 * | 7/2002 | Watanabe et al. | ............. | 378/197 |
| 6,422,747 B2 * | 7/2002 | Akutsu et al. | ................. | 378/198 |
| 6,430,259 B2 * | 8/2002 | Meek et al. | ..................... | 378/117 |
| 6,789,940 B2 * | 9/2004 | Meyer et al. | .................. | 378/196 |
| 6,830,375 B2 * | 12/2004 | Deshpande | .................... | 378/197 |
| 6,871,715 B1 * | 3/2005 | Diaz Carmena et al. | .. | 180/65.51 |
| 7,029,175 B2 * | 4/2006 | Karaus et al. | ................. | 378/197 |
| 7,046,764 B1 * | 5/2006 | Kump | ........................... | 378/117 |
| 7,093,976 B2 * | 8/2006 | Fadler et al. | .................. | 378/197 |
| 7,160,027 B2 * | 1/2007 | Bauer et al. | ................... | 378/197 |
| 7,175,346 B2 * | 2/2007 | Heinze et al. | ................. | 378/197 |
| 7,278,785 B2 * | 10/2007 | Fadler et al. | .................. | 378/197 |
| 7,486,767 B2 * | 2/2009 | Sonobe et al. | .................. | 378/39 |
| 7,602,882 B2 * | 10/2009 | Dorre | ............................. | 378/117 |
| 7,609,813 B2 * | 10/2009 | Curtis | ............................. | 378/91 |
| 7,764,767 B2 * | 7/2010 | Beimler et al. | ............... | 378/117 |
| 8,201,999 B2 * | 6/2012 | Uchida et al. | ................. | 378/197 |

FOREIGN PATENT DOCUMENTS

| | | |
|---|---|---|
| JP | 2000-316838 | 11/2000 |
| JP | 2001-106082 | 4/2001 |
| JP | 2007-244569 | 9/2007 |
| JP | 2009-005909 | 1/2009 |

\* cited by examiner

*Primary Examiner* — Allen C. Ho
(74) *Attorney, Agent, or Firm* — Jean C. Edwards, Esq.; Edwards Neils PLLC

(57) ABSTRACT

A judging section judges whether the operating portion provided on a device is being operated. A correcting section performs correction such that the values of signals S that indicate the intensities and directions of external forces applied to the operating portion, which are output from a detecting section while it is judged that the operating portion is not being operated, are included in a dead zone range with respect to control of a movement assisting section that assists manual movement of the device by urging the device. A control section controls the movement assisting section to assist movement in the directions of the external forces indicated by the signals output by the detecting section, and to not perform movement assistance in the case that the signal values are included in the dead zone range.

17 Claims, 11 Drawing Sheets

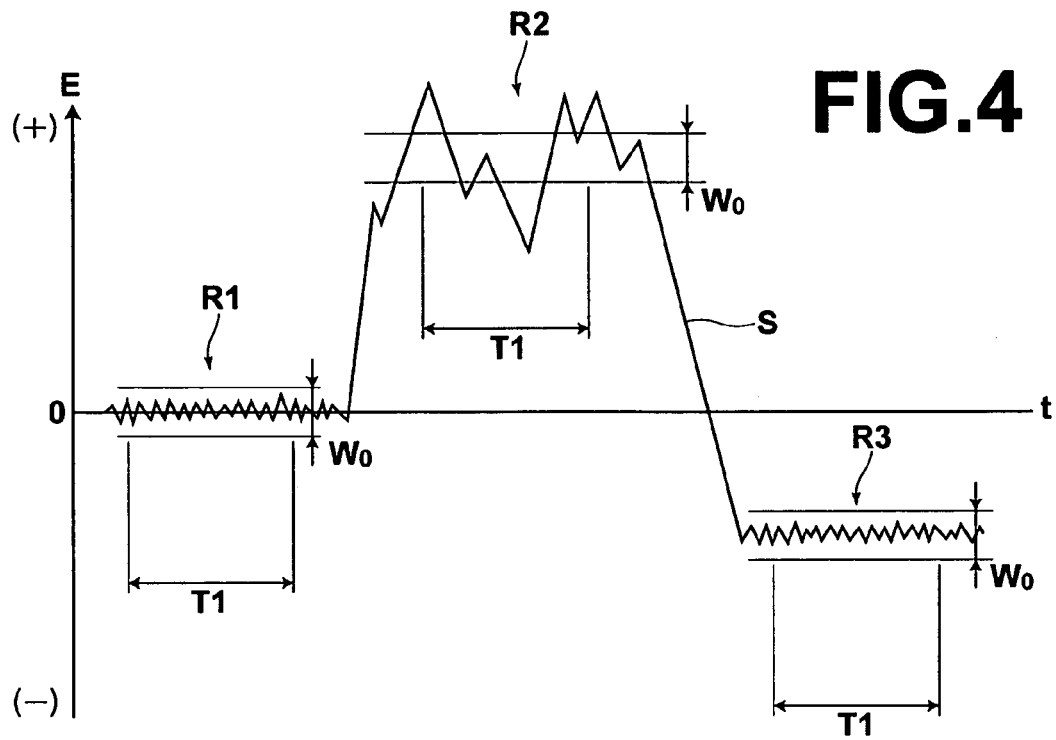
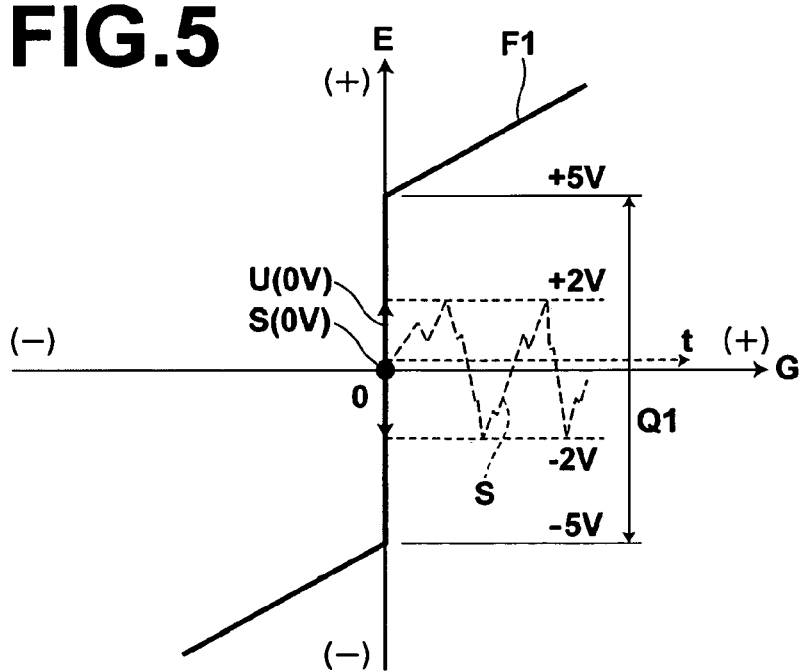

RADIATION IMAGING APPARATUS WITH ASSISTED MOVEMENT

CROSS-REFERENCE TO RELATED APPLICATIONS

The present application claims priority from Japanese Patent Application No. 2009-043526, filed Feb. 26, 2009, and Japanese Patent Application No. 2009-192771, filed Aug. 24, 2009, the contents of all of which are herein incorporated by reference in their entirety.

BACKGROUND OF THE INVENTION

1. Field of the Invention

The present invention is related to a radiation imaging apparatus. More specifically, the present invention is related to a radiation imaging apparatus that urges a device to be employed in radiation images, to assist manual movement of the device.

2. Description of the Related Art

Conventionally, it is uncommon for small scale medical facilities, such as physicians in private practice and clinics, to install radiation imaging apparatuses dedicated to imaging specific portions of subjects. These medical facilities generally employ a single radiation imaging apparatus to perform radiation imaging of various body parts as necessary. For example, radiation imaging systems, in which an upright imaging table and a supine imaging table are installed in a single imaging room, a radiation source is supported by a ceiling runner suspension device or the like, and the irradiation direction of radiation is adjusted to be toward the upright imaging table and the supine imaging table by moving or changing the orientation of the radiation source, are known (refer to Japanese Unexamined Patent Publication Nos. 2009-005909 and 2007-244569).

There is also a known radiation imaging apparatus of the type described above, in which an operating handle is integrally formed with a device such as a radiation source, and when external forces are applied to the operating handle, the device is urged in the directions of the external forces to assist manual movement (hereinafter, this assistance will also be referred to as "power assistance") of the device (refer to Japanese Unexamined Patent Publication No. 2000-316838).

In addition, there is a known apparatus that performs control of such power assistance such that a dead zone is provided (refer to Japanese Unexamined Patent Publication No. 2001-106082). For example, the external forces which are applied to the operating handle are measured, and the device is urged only when the measured external forces are greater than a predetermined value. By exerting control such that the dead zone is provided, unnecessary movement of the device due to inadvertent light contact with the operating handle or slight externally applied vibrations can be prevented.

Further, there is a known radiation imaging apparatus that executes the movement assistance by subtracting the weight of the operating handle itself from the external forces applied thereto, to more accurately perform control of the power assistance (refer to Japanese Unexamined Patent Publication No. 2000-316838). The control of the power assistance in this apparatus corrects the urging force used for power assistance, employing the inclination angle and the weight of the operating handle which is integrally formed with the device to be assisted in movement, which are stored in advance, to improve the operability when users move the device.

There are cases in which the settings for dead zones with respect to control of power assistance shift over time, due to changes in environment, and the like. That is, there are cases in which a dead zone range, which is initially set such that the power assistance urging force is generated when external forces exceeding 500 gf is applied onto an operating portion such as an operating handle from either the right or the left, shifts such that the power assistance urging force is generated when an external force applied from the left exceeds 700 gf and when an external force applied from the right exceeds 300 gf, for example. In cases that this type of shifting of dead zones occur, users sense the change in operability when moving the device with which the operating portion is integrally formed.

Further, if the shifting in the dead zone becomes great, there is a possibility that the power assistance urging force will be generated even when external force is not being applied to the operating section, resulting in the device to which the operating portion is mounted from moving in an uncontrolled manner.

In order to correct shifts in dead zones, it is necessary to interrupt radiation imaging to perform correction.

For this reason, there is demand to enable correction of shifts in dead zones with respect to control of power assistance without interrupting radiation imaging.

SUMMARY OF THE INVENTION

The present invention has been developed in view of the foregoing circumstances. It is an object of the present invention to provide a radiation imaging apparatus that can suppress deterioration in quality of movement assistance that employs an operating portion, without decreasing the imaging efficiency of radiation imaging.

A radiation imaging apparatus of the present invention comprises:

movement assisting means, for assisting manual movement of a device which is employed to perform radiation imaging, by urging the device;

an operating portion that enables operation of the movement of the device, which is assisted by the movement assisting means;

detecting means, for detecting external forces which are applied to the operating section, and outputs signals indicating the intensities and directions of the external forces;

control means, for controlling the movement assisting means to assist movement of the device in the directions of the external forces indicated by the signals output from the detecting means, and for controlling the movement assisting means to not assist manual movement of the device when the values of the signals are included within a dead zone range;

judging means, for judging whether the operating portion is being operated; and correcting means, for performing corrections such that the values of signals, which are obtained while it is judged that the operating portion is not being operated, are included in the dead zone range with respect to control exerted by the control means.

Note that the dead zone range refers to the range of a dead zone with respect to control of the movement assisting means. That is, the dead zone range is a range which is determined such that the control means does not respond to signal values output by the detecting means for detecting the external forces applied to the operating portion therein. Accordingly, assistance of movement by the movement assisting means is not executed if the values of the signals output from the detecting means are within the dead zone range.

The expression "performing corrections such that the values of signals, which are obtained while it is, judged that the operating portion is not being operated, are included in the dead zone range with respect to control exerted by the control means" means that the upper limit value and the lower limit value of the signals, which are output from the detecting means while it is judged that the operating portion is not being operated, are both included within the dead zone range with respect to control exerted by the control means.

The judging means may judge that the operating portion is not being operated when the values of signals which are output from the detecting means are constant.

The judging means may judge that the operating portion is not being operated when the fluctuating range of the signals which are output from the detecting means is a predetermined range or less, and judge that the operating portion is being operated when the fluctuating range of the signals which are output from the detecting means is greater than the predetermined range. Note that it is desirable for the judging means to judge that the operating portion is not being operated when the fluctuating range of the signals which are output form the detecting means over a predetermined amount of time or greater is the predetermined range or less.

The judging means may judge that the operating portion is not being operated when the fluctuation of the signals which are output from the detecting means are repetitions of the same fluctuation pattern, and judge that the operating portion is being operated when the fluctuation of the signals which are output from the detecting means are not repetitions of the same fluctuation pattern.

The correcting means may perform corrections such that a signal value corresponding to the center of the fluctuating range of the signals, which are output from the detecting means while it is judged that the operating portion is not being operated, corresponds to the center of the dead zone range with respect to control exerted by the control means. Note that the signal value corresponding to the center of the fluctuating range of the signals output from the detecting means may be a value at the midpoint between the maximum signal value and the minimum signal value.

The correcting means may perform corrections such that an average value of the signals, which are output from the detecting means while it is judged that the operating portion is not being operated, corresponds to the center of the dead zone range with respect to control exerted by the control means.

The correcting means may correct at least one of the center, the upper limit, and the lower limit of the dead zone such that both the upper limit value and the lower limit value of the signals, which are output from the detecting means while it is judged that the operating portion is not being operated, are included in the dead zone range.

The correcting means may change the width of the dead zone range according to the fluctuation range of the signals, which are output from the detecting means while it is judged that the operating portion is not being operated.

The correcting means may administer correction on at least one of the signals which are output from the detecting means and the control properties of the control means. Note that the correcting means may change the output properties of the detecting means or the input properties of the control means to administer correction such that the values of signals, which are obtained while it is judged that the operating portion is not being operated, are included in the dead zone range with respect to control exerted by the control means.

The movement assisting means may assist movement of the device in the vertical and horizontal directions, while supporting the device in a state in which the device is suspended from the ceiling of a room.

The device may be capable of changing its orientation with respect to the movement assisting means.

The device may be one of a radiation source to be employed in radiation imaging and a radiation detector to be employed in radiation imaging.

The radiation imaging apparatus of the present invention is equipped with the judging means, for judging whether the operating portion is being operated; and the correcting means, for performing corrections such that the values of signals, which are obtained while it is judged that the operating portion is not being operated, are included in the dead zone range with respect to control exerted by the control means. Therefore, deterioration in quality of movement assistance that employs the operating portion can be suppressed, without decreasing the imaging efficiency of radiation imaging.

That is, the operating portion is not constantly being operated by external forces during radiation imaging. There are times during radiation imaging that the operating portion is not being operated, and no external force is being applied thereto. Therefore, the judging means judges whether external forces are being applied to the operating portion during radiation imaging. Signals (that indicate the intensity and direction of external forces applied to the operating portion) which are output from the detecting means while external forces are not being applied to the operating portion, that is, while the operating portion is not being operated are obtained, and the correcting means designates the values of these signals to be within the dead zone range. Thereby, correction is automatically performed such that the power assist urging force is not generated when external forces are not being applied to the operating portion, regardless of whether radiation imaging is being performed. Therefore, deterioration in quality of movement assistance that employs the operating portion can be suppressed, without decreasing the imaging efficiency of radiation imaging.

A configuration may be adopted, wherein the judging means judges that the operating portion is not being operated when the values of signals which are output from the detecting means are constant. In this case, whether the operating portion is being operated can be judged more positively.

A configuration may be adopted, wherein the judging means judges that the operating portion is not being operated when the fluctuating range of the signals which are output from the detecting means is a predetermined range or less, and judges that the operating portion is being operated when the fluctuating range of the signals which are output from the detecting means is greater than the predetermined range. Alternatively, a configuration may be adopted, wherein the judging means judges that the operating portion is not being operated when the fluctuation of the signals which are output from the detecting means are repetitions of the same fluctuation pattern, and judges that the operating portion is being operated when the fluctuation of the signals which are output from the detecting means are not repetitions of the same fluctuation pattern. In both these cases, whether the operating portion is being operated can be judged more positively.

A configuration may be adopted, wherein the correcting means performs corrections such that a signal value corresponding to the center of the fluctuating range of the signals, which are output from the detecting means while it is judged that the operating portion is not being operated, corresponds to the center of the dead zone range with respect to control exerted by the control means. Alternatively, a configuration may be adopted, wherein the correcting means performs corrections such that an average value of the signals, which are output from the detecting means while it is judged that the operating portion is not being operated, corresponds to the center of the dead zone range with respect to control exerted by the control means. In both these cases, deterioration in quality of movement assistance that employs the operating portion can be more positively suppressed.

That is, a dead zone range in a first direction, that is, a range of external forces in the first direction that when applied does not cause the movement assisting means to generate urging forces, and a dead zone range in a second direction opposite the first direction, that is, a range of external forces in the second direction that when applied does not cause the movement assisting means to generate urging forces, can be corrected to be approximately equal. Thereby, differences in operability (operating sensation) when urging forces are generated by users moving the operating portion in the first and second directions can be reduced, and deterioration in quality of movement assistance that employs the operating portion can be suppressed.

BRIEF DESCRIPTION OF THE DRAWINGS

FIG. 4 is a graph that illustrates values of signals, which are detected and output by a detecting section.

FIG. 5 is a graph that illustrates a state in which the relationship between signals during non operative periods and a control dead zone range is correct.

DESCRIPTION OF THE PREFERRED EMBODIMENTS

Figure 1:
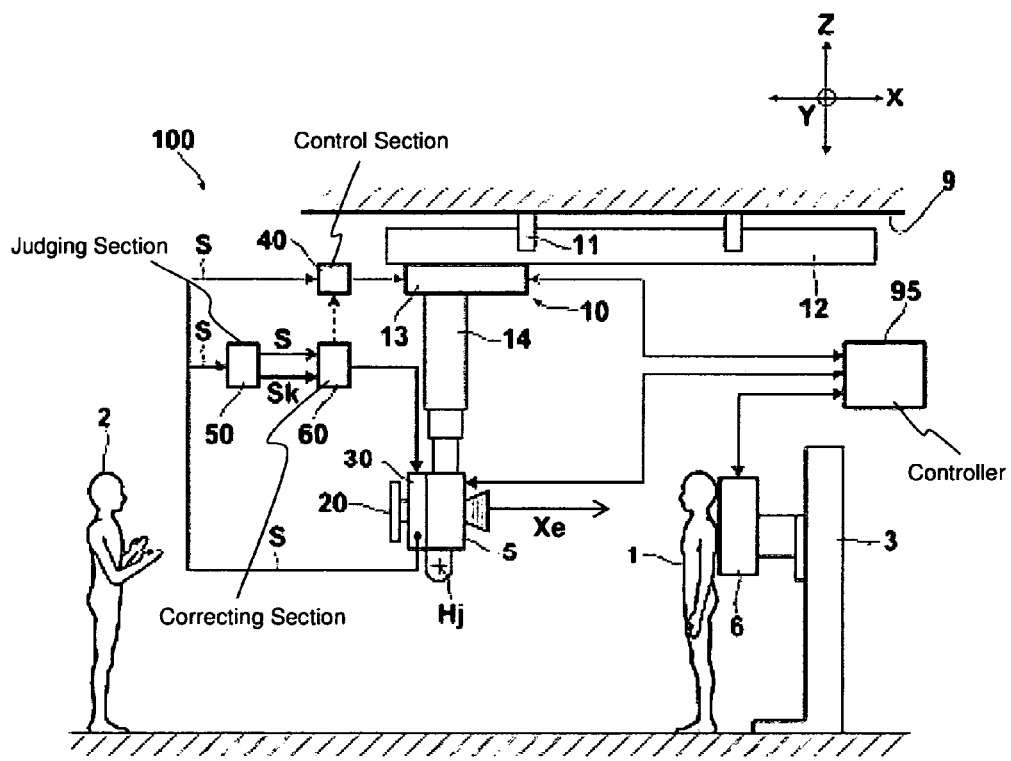
FIG. 1 is a diagram that schematically illustrates the structure of a suspended radiation imaging apparatus according to an embodiment of the present invention in the case that upright radiation imaging is to be performed.
Figure 2:
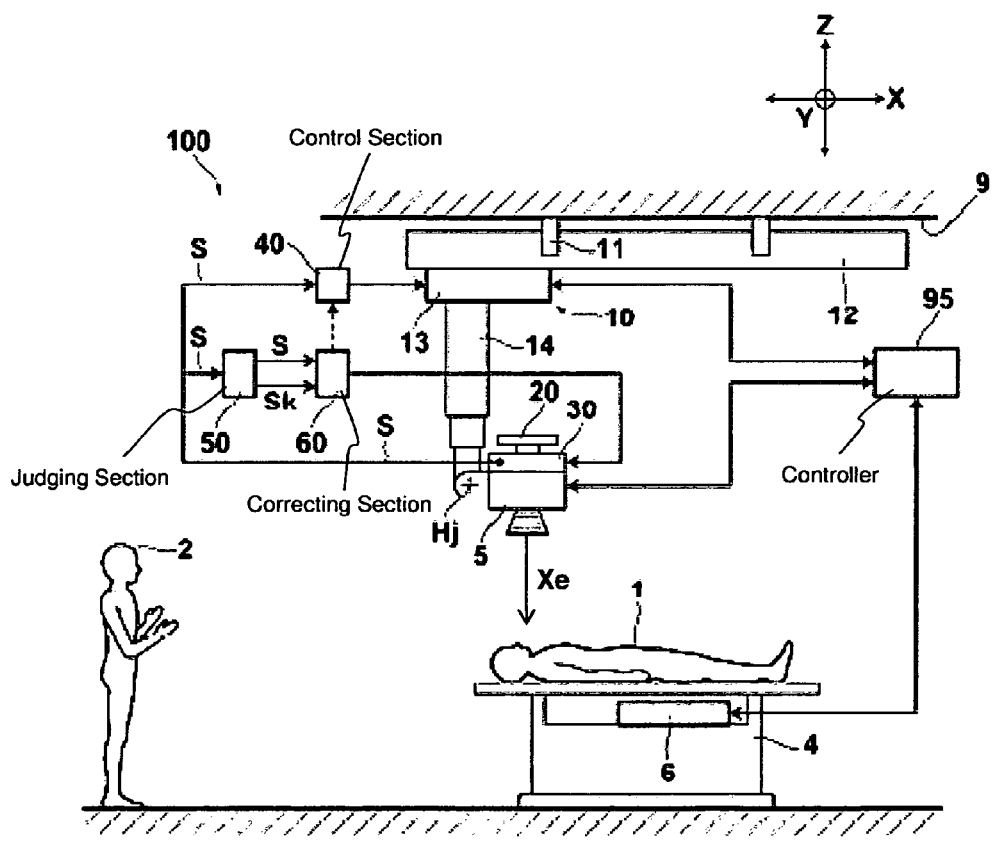
FIG. 2 is a diagram that schematically illustrates the structure of a suspended radiation imaging apparatus according to the embodiment of the present invention in the case that supine radiation imaging is to be performed.
Figure 3:
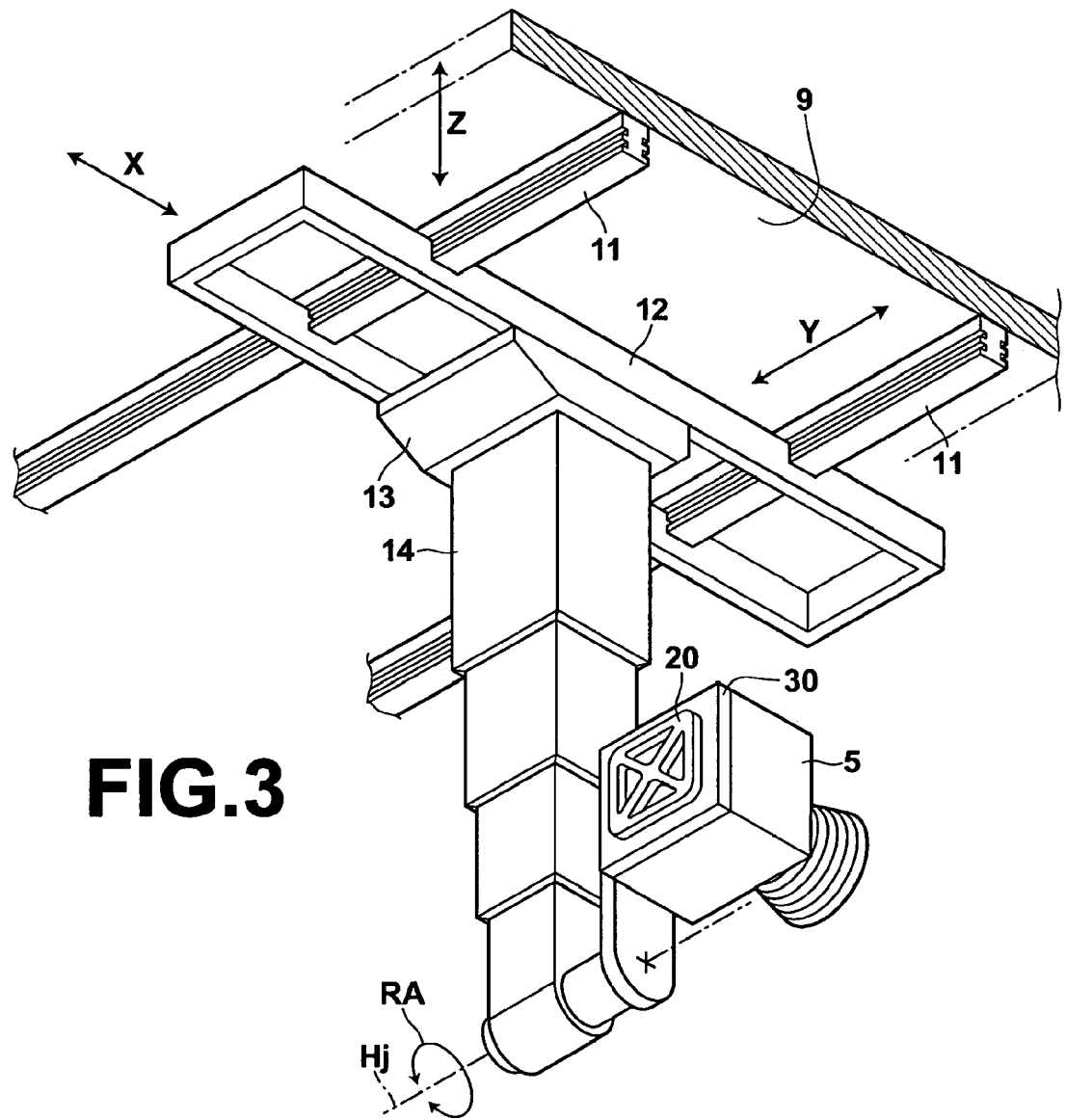
FIG. 3 is a magnified perspective view of a movement assisting section.

Hereinafter, embodiments of the present invention will be described with reference to the attached drawings. FIGS. 1 and 2 are diagrams that schematically illustrate the structure of a suspended radiation imaging apparatus 100 according to an embodiment of the present invention. FIG. 1 is a side view that illustrates a case in which upright radiation imaging is performed, and FIG. 2 is a side view that illustrates a case in which supine radiation imaging is performed. FIG. 3 is a magnified perspective view of a movement assisting section that functions as a movement assisting means.

As illustrated in FIGS. 1, 2, and 3, the radiation imaging apparatus 100 is a radiation imaging apparatus which is suspended from the ceiling of a room. The radiation imaging apparatus 100 is equipped with: a radiation source 5, which is a device to be employed in radiation imaging; a radiation detector 6, for detecting radiation which is irradiated by the radiation source 5 and passes through a subject 1; a movement assisting section 10, for urging the radiation source 5 in the vertical and horizontal directions while supporting the radiation source 5 in a state in which the device is suspended from the ceiling 9 of a room, to assist manual movement of the radiation source 5 by an operator 2; an operating handle 20, which is integrally formed with the radiation source 5, for operating the movement of the radiation source 5 that receives assistance from the movement assisting section 10; and a detecting section 30, for detecting external forces which are applied to the operating handle 20 and outputs signals S that indicate the intensity and direction of the external forces.

The movement assisting section 10 urges the radiation source 5 to reduce the amount of necessary external force which is applied to the operating handle 20 by the operator 2 when moving the radiation source 5. That is, the movement assisting section 10 assists movement of the radiation source 5 by the operator 2.

Note that the orientation of the radiation source 5 with respect to the movement assisting section 10 is changeable. Because the radiation source 5 weighs approximately 250 kg, it is not easy to move the radiation source 5 by manual strength alone.

More specifically, the movement assisting section 10 is equipped with fixed rails 11 which are provided on the ceiling 9; a movable rail 12 that extends in a direction perpendicular to the direction that the fixed rails 11 extend in, and is capable of moving in the direction that the fixed rails 11 extend in (the direction indicated by arrow Y in FIG. 3) while being suspended by the fixed rails 11; a horizontally moving base 13 which is capable of moving in the direction that the movable rail 12 extends in (the direction indicated by arrow X in FIG. 3) while being suspended by the movable rail 12; a support column 14 which is mounted to the horizontally moving base 13 and is capable of moving in the vertical direction (the direction indicated by arrow Z in FIG. 3) by telescopic motion; and drive motors (not shown) for driving the movable rail 12 in the Y direction, for driving the horizontally moving base 13 in the X direction, and for extending and contracting the support column 14.

The radiation source 5 is mounted to the lower end of the support column 14. The radiation source 5 is capable of changing its orientation with respect to the support column 14. The radiation source 5 is mounted on the support column 14 so as to be rotatable about a horizontal axis Hj (in the direction indicated by arrow RA of FIG. 3) in order to enable both upright radiation imaging and supine radiation imaging.

Here, the operating handle 20 is integrally mounted onto the radiation source 5 via the detecting section 30. The detecting section 30 detects the intensity and direction of external forces which are applied to the operating handle 20. The detecting section 30 detects forces which are applied in each of the X direction, the Y direction, and the Z direction, or forces (rotational moments) applied about the X direction axis, the Y direction axis, and the Z direction axis, to detect the direction and intensity of external forces which are applied to the operating handle 20.

The radiation imaging apparatus 100 is further equipped with a control section 40, for controlling the movement assisting section 10 to assist movement of the radiation source 5 in the directions of the external forces indicated by the signals S output from the detecting section 30, and for controlling the movement assisting section 10 to not assist manual movement of the radiation source 5 when the values of the signals S are included within a dead zone range with respect to control of the movement assisting section 10.

The dead zone with respect to control of the movement assisting section 10 is set such that the control section 40 is not sensitive to external forces less than or equal to a predetermined intensity, which are applied to the operating handle 20. That is, the dead zone is set such that the assistance is not performed with respect to applied external forces that fall within the dead zone, by the control section 40 controlling the movement assisting section 10 to assist movement of the radiation source 5.

Further, the radiation imaging apparatus 100 is equipped with: a judging section 50, for judging whether the operating handle 20 is being operated; and a correcting section 60 for performing corrections such that the values of signals S, which are obtained while it is judged that the operating handle 20 is not being operated (hereinafter, also referred to as "non operative state signals S"), are included in the dead zone range with respect to control exerted by the control section 40.

That is, the correcting section 60 performs corrections such that the values of the non operative state signals S output from the detecting section 30 are included within the dead zone range with respect to control exerted by the control section 40. Here, the correcting section 60 adjusts the output properties of the detecting section 30, such that the control section 40 is not sensitive to fluctuating values of the non operative state signals S, even in cases that the values of the non operative state signals S fluctuate. More specifically, the correcting section 60 adjusts the output properties of the detecting section 30 by shifting the values of the non operative state signals S output from the detecting section 30 such that the fluctuating values of the non operative state signals S are included within the dead zone range.

Here, the correcting section 60 increases or decreases the values of the non operative state signals S, which are output from the detecting section 30 while it is judged that the operating handle 20 is not being operated, by a constant amount, to change the output properties of the detecting section 30. Thereby, the values of the non operative state signals S output from the detecting section 30 are included in the dead zone range with respect to control exerted by the control section 40.

Note that it is desirable for the correcting section 60 to perform correction such that an average value of the non operative state signals S or a signal value corresponding to the center of the fluctuating range of the non operative state signals S, which are output from the detecting section 30 while it is judged that the operating handle 20 is not being operated, corresponds to the center of the dead zone range with respect to control exerted by the control section 40.

Here, the signal value corresponding to the center of the fluctuating range of the non operative state signals S may be a value at the midpoint between the maximum value and the minimum value of the non operative state signals S (midpoint=(maximum value+minimum value)/2).

Further, the correcting section may correct the control properties of the control section 40, by changing the width of the dead zone range according to the fluctuation range of the non operative state signals S.

Note that the fluctuations in the non operative state signals S are caused due to vibrations of the building in which the radiation imaging apparatus 100 is installed, air conditioning system within the building, and the like.

The judging section 50 judges whether the operating handle 20 is being operated, employing the signals which are output from the detecting section 30.

The judging section 50 judges that the operating handle 20 is not being operated when the fluctuating range of the signals S which are output from the detecting section 30 within a predetermined amount of time is a predetermined range or less, and judges that the operating handle 20 is being operated when the fluctuating range of the signals S which are output from the detecting section 30 is greater than the predetermined range.

Alternatively, the judging section 50 may judge that the operating handle 20 is not being operated when the fluctuation of the signals S which are output from the detecting section 30 are repetitions of the same fluctuation pattern, and may judge that the operating handle 20 is being operated when the fluctuation of the signals S which are output from the detecting section 30 are not repetitions of the same fluctuation pattern. As a further alternative, the judging section 50 may judge that the operating handle 20 is not being operated when the values of signals S which are output from the detecting section 30 do not fluctuate and are constant.

FIG. 4 illustrates the judgment method employed by the judging means 50, and is a graph having the values (voltages) of the signals S detected and output by the detecting section 30 plotted on a horizontal axis t that represents time and a vertical axis E that represents voltage.

Note that the signals S represent the intensity and direction of the external forces applied to the operating handle 20 as described above. For example, external forces which are applied in the rightward, forward, and upward directions are indicated by positive voltages, and external forces which are applied in the leftward, backward, and downward directions are indicated by negative voltages in a calibrated standardized state. The intensities of the applied external forces can be represented by the absolute values of the voltages.

As illustrated in region R1 of FIG. 4, the judging section 50 judges that the operating handle 20 is not being operated when the fluctuation of voltages represented by the signals S are a predetermined range Wo or less over a predetermined amount of time T1, for example.

Meanwhile, as illustrated in region R2 of FIG. 4, the judging section 50 judges that the operating handle 20 is being operated when the fluctuation of voltages represented by the signals S are greater than the predetermined range Wo over the predetermined amount of time T1.

Note that as illustrated in region R3 of FIG. 4, the judging section 50 judges that the operating handle 20 is not being operated when the fluctuation of voltages represented by the signals S are less than or equal to the predetermined range Wo, even when the voltages are shifted parallel from the voltages at region R1.

There are cases in which the values of the non operative signals S detected by the detecting section 30 change, accompanying changes in orientation of the radiation source 5 and consequently the operating handle 20, for example. However, even in these cases, the fluctuating range of the values of the non operative state signals S does not change. Thereby, the judging section 50 is capable of accurately judging whether the operating handle 20 is being operated, regardless of the orientation of the operating handle. The operation when the orientation of the radiation source 5 is changed will be described later.

Note that the fluctuating range of the voltage values represented by the non operative state signals S may be derived as the difference between the maximum voltage value and the minimum voltage value. Alternatively, the fluctuating range may be derived by statistically processing deviations of signal values from an average value of the fluctuating voltages.

Note that synchronization of the apparatus as a whole and the operational timing of each component are controlled by a controller 95.

Next, an operation in which the radiation imaging apparatus 100 of the present embodiment is employed to perform upright radiation imaging will be described.

The operator 2 who executes upright radiation imaging prompts the subject 1 to stand toward the front surface of the radiation detector 6, which is supported by an upright imaging base 3 (refer to FIG. 1). Note that when performing supine radiation imaging, the subject 1 is placed in a supine position toward the front surface of the radiation 6, which his provided on a horizontal imaging base 4 (refer to FIG. 2).

Next, the operator 2 grips the operating handle 20, which is formed integrally with the radiation source 5, and applies external force to the handle 20, in the direction that the radiation source 5 is to be moved.

The intensity and the direction of the external force which is applied to the operating handle 20 are detected by the detecting section 30. The signals S that indicate the intensity and the direction of the external force are continuously input to the judging section 50 and the control section 40.

When the values of the signals S which are input to the control section 40 are within the dead zone range with respect to control exerted by the control section 40, the control section 40 controls the movement assisting section 10 such that movement of the radiation source 5 is not assisted. On the other hand, when the values of the signals S are outside the dead zone range with respect to control, the control section 40 controls the drive motors of the movement assisting section 10 to urge the radiation source 5 in the direction indicated by the signals S.

Thereby, the radiation source 5 is moved by receiving the urging force form the movement assisting section 10 and the external force applied by the operator 2 via the operating handle 20 simultaneously.

The movement assisting section 10 urges the radiation source 5, which weighs 250 kg, in the vertical and horizontal directions according to control exerted by the control section corresponding to operations of the operating handle 20 by the operator 2 in this manner. Thereby, the operator 2 can easily move the radiation source 5 to desired positions.

When radiation imaging is to be performed, the radiation source 5, the radiation detector 6, and the subject 1 are placed at predetermined positions. Then, the operator 2 inputs commands to execute radiation imaging to each component via the controller 95. Thereby, radiation Xe, which is emitted from the radiation source 5, passes through the subject 1 and is detected by the radiation detector 6.

The radiation detector 6 outputs image signals that represent a radiation image of the subject 1, which is detected by the radiation detector 6, and radiation imaging using the radiation imaging apparatus 100 is completed.

Note that the signals that indicate the intensity and direction of external forces which are applied to the operating handle 20 are constantly being input to the judging section 50, even during execution of the radiation imaging. The judging section 50 continuously judges whether the operating handle 20 is being operated, and outputs signals Sk that indicate the results of judgment and the signals S to the correcting section 60.

The correcting section 60 changes the output properties of the detecting section 30 such that a signal value corresponding to the center of the fluctuating range of the non operative state signals S, which are output from the detecting section 30 while that the operating handle 20 is not being operated, corresponds to the center of the dead zone range with respect to control exerted by the control section 40 when the judgment signals Sk that indicate that the operating handle 20 is not being operated are input thereto, even during execution of the radiation imaging.

Next, the correction which is performed by the correcting section 60 will be described in detail with reference to FIGS. 5 through 7.

Figure 6:
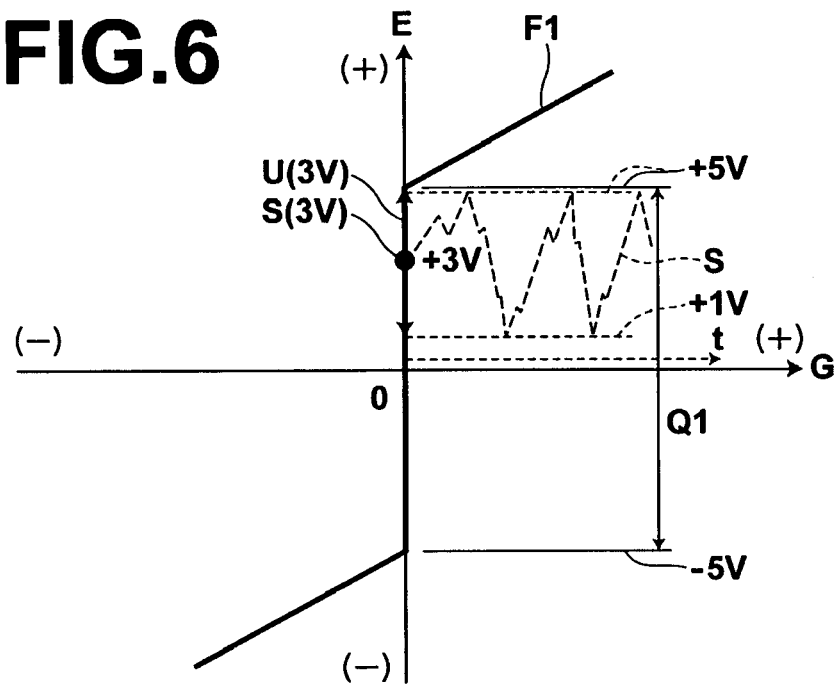
FIG. 6 is a graph that illustrates a state in which the relationship between signals during non operative periods and a control dead zone range is shifted.
Figure 7:
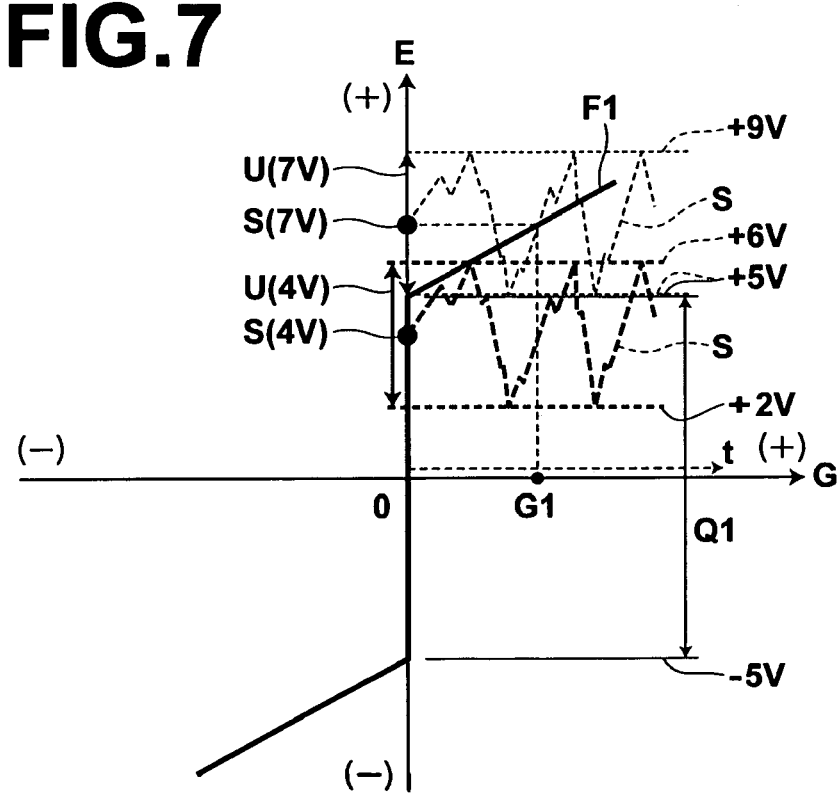
FIG. 7 is a graph that illustrates a state in which the relationship between signals during non operative periods and a control dead zone range is greatly shifted.

FIGS. 5 through 7 are graphs having voltages E as their vertical axes and forces G as their horizontal axes, that illustrate relationships between voltages which are the values of the signals S and the urging forces generated by the movement assisting section 10 under control of the control section 40. Control property curves that represent the relationships between the voltages and the urging forces are denoted by reference numerals F1. The ranges of dead zones with respect to control are denoted by reference numerals Q1.

In addition, the average values of the fluctuating non operative state signals S are denoted by reference numerals S (0V), S (3V), S (7V), and S (4V) in FIGS. 5 through 7.

Further, the fluctuating ranges of the voltage values of the non operative state signals S are denoted by reference numerals U (0V), U (3V), U (7V), and U (4V) in FIGS. 5 through 7. The fluctuations of the voltage values of the non operative state signals S are illustrated by broken lines along temporal axes t in FIGS. 5 through 7.

Note that the fluctuating range of the voltage values of the non operative state signals S is 4V±2V in FIGS. 5 through 7.

FIG. 5 is a graph that illustrates a state in which the relationship between the values of the non operative state signals S which are output from the detecting section 30 and a dead zone range Q with respect to control exerted by the control section 40 are in a desirable state. The values of the non operative state signals S are within the dead zone range, and the average value of the non operative state signals S corresponds to the center of the dead zone range Q.

More specifically, the fluctuating range ±2V (indicated by arrows U (0V) in FIG. 5) of the voltage values of the non operative state signals S which are output from the detecting section 30 while it is judged that the operating handle 20 is not being operated is within the dead zone range of ±5V. In addition, the average value of the non operative state signals S (the value denoted as S (0V) in FIG. 5) is at the center of the dead zone range of ±5V.

In the case that the relationship between the values of the non operative state signals S output from the detecting section 30 and the dead zone range Q of the control section 40 are set in this manner, the assistance in moving the radiation source 5 provided by the movement assisting section 10 is initiated when the same amount of force is applied to the operating handle 20 in either the forward or backward directions. Therefore, the movement assistance employing the operating handle 20 exhibits favorable operability.

Here, the correcting section 60 attempts to perform corrections such that the average value of the voltages of the non operative state signals S corresponds to 0V, which is the center of the dead zone range with respect to control exerted by the control section 40. However, because the average value of the voltages of the non operative state signals S is already 0V, the relationship between the values of the non operative state signals S output from the detecting section 30 and the dead zone range Q of the control section 40 does not change. Accordingly, even if correction is administered by correcting section 60 in this state, the operability related to movement assistance by the movement assisting section 10 does not change.

FIG. 6 is a graph that illustrates a case in which the average value of the non operative state signals S is shifted from the center of the dead zone range with respect to control, but the values of the fluctuating non operative state signals S are included within the dead zone range.

More specifically, the average value (the value denoted as S (3V) in FIG. 6) of the voltages of the non operative state signals S, which are obtained while it is judged that the operating handle is not being operated, is +3V, which is shifted from the center of the dead zone range of ±5V. However, the fluctuating range of +1V through +5V (indicated by arrow U (3V) in FIG. 6) is included in the dead zone range of ±5V.

In this case, the assistance in moving the radiation source 5 by the movement assisting section 10 provides assistance of the urging force even with a slight amount of external force when the operating handle 20 is pressed forward. However, when the operating handle 20 is pulled backward, a greater amount of force than that which is applied to initiate movement assistance in the forward direction is required for the urging force to be generated in the backward direction. Therefore, the operability related to movement assistance employing the operating handle deteriorates somewhat. However, driving forces being generated by the movement assisting section 10 even when no external force is being applied to the operating handle 20, resulting in the radiation source 5 moving in an uncontrolled manner, can be prevented.

Note that in the case that the correcting section 60 is that which administers corrections such that the values of the non operative state signals S are included in the dead zone range with respect to control when the judging section 50 judges that the operating handle 20 is not being operated, because the fluctuating range of the values of the non operative state signals S (+1V through +5V) is already included in the dead zone range of ±5V, the relationship between the values of the non operative signals S and the dead zone range Q will not change, even if correction is administered. Accordingly, even if correction is administered by such a correcting section 60, the operability of the movement assistance provided by the movement assisting section 10 will not change.

However, the correcting section 69 may correct the output properties of the detecting section 30 such that the average voltage value +3V of the non operative signals S corresponds to 0V, which is the center of the dead zone range Q with respect to control by the control section 40. In this case, the relationship between the control dead zone Q and the non operative signals S can be corrected to a desirable state, that is, the state described with reference to FIG. 5.

FIG. 7 is a graph that illustrates a case in which the fluctuating range of the values of the non operative state signals S is shifted outside the dead zone range.

More specifically, FIG. 7 illustrates a case in which the average value of the voltage of the non operative state signals S (+7V, refer to S (7V) in FIG. 7) is outside the dead zone range with respect to control of ±5V. In addition, the fluctuating range of the voltage values of the non operative state signals S (+5V through +9V, refer to U (7V) in FIG. 7) is completely outside the dead zone range with respect to control of ±5V.

The assistance in moving the radiation source 5 provided by the movement assisting section 10 in such a case results in an urging force indicated by G1 in FIG. 7 being generated when the voltage value of the non operative state signal S is +7V, for example. That is, there is a possibility that the radiation source 5 will move in an uncontrolled manner due to this urging force.

Here, the judging section 50 can correctly judge whether the operating handle 20 is being operated, even during uncontrolled movement of the radiation source 5 due to the urging force provided by the movement assisting section 10. Therefore, the correcting section 60 administers correction such that the values of the non operative state signals S, which are output from the detecting section 30 while it is judged that the operating handle 20 is not being operated, are included in the dead zone range Q with respect to control by the control section 40. Thereby, the uncontrolled movement of the radiation source can be ceased. For example, the correcting section 60 corrects the output properties of the detecting section 30 such that the average voltage value of the non operative state signals S (+7V) output from the detecting section 30 corresponds to 0V, which is the center of the dead zone range Q (refer to FIG. 5), or to 3V (refer to FIG. 6), to correct the voltage values of the non operative state signals S. Thereby, the fluctuating range of the non operative state signals S can be included in the dead zone range with respect to control by the control section 40 of ±5V, and uncontrolled movement of the radiation source 5 can be ceased. That is, correction can be administered such that the settings are the same as those described above with reference to FIG. 5 and FIG. 6.

Correction similar to that described above is also administered in the case that the average value of the voltage of the non operative state signals S (+4V, refer to S (4V) in FIG. 7) is within the dead zone range with respect to control of ±5V, and only a portion of the fluctuating range of the voltage values of the non operative state signals S (+2V through +6V, refer to U (4V) in FIG. 7) is within the dead zone range with respect to control of ±5V. That is, the correcting section 60 corrects the output properties of the detecting section 30 such that the average voltage value of the non operative state signals S (+4V) output from the detecting section 30 corresponds to 0V, which is the center of the dead zone range Q (refer to FIG. 5), or to 3V (refer to FIG. 6), to correct the voltage values of the non operative state signals S. Thereby, the fluctuating range of the non operative state signals S can be included in the dead zone range with respect to control by the control section 40 of ±5V, and uncontrolled movement of the radiation source 5 can be ceased. That is, correction can be administered such that the settings are the same as those described above with reference to FIG. 5 and FIG. 6.

As described above, the correcting section 60 can administer corrections even while the radiation source 5 is moving. Further, the radiation imaging apparatus 100 may be configured such that the correcting section 60 administers corrections only when the radiation source 5 is moving, in order to prevent uncontrolled movement of the radiation source 5.

Note that in the above descriptions with reference to FIGS. 5 through 7, the average values of the non operative state signals was employed as the signal value corresponding to the center of the fluctuating range of the non operative state signals output from the detecting section 30. Alternatively, the signal value corresponding to the center of the fluctuating range of the non operative state signals may be a value at the midpoint between the maximum value and the minimum value thereof.

Note that in the above descriptions with reference to FIGS. 5 through 7, the correcting section 60 corrected the output properties of the detecting section 30 to correct the values of the signals output from the detecting section 30, such that the values of the non operative state signals are included in the dead zone range. However, the present invention is not limited to this configuration, and the correcting section 60 may correct the control properties (input properties) of the control section 40 such that such that the values of the non operative state signals output from the detecting section 30 are included in the dead zone range.

Next, a case in which the correcting section 60 administers correction to narrow the dead zone range with respect to control will be described.

Figure 8:
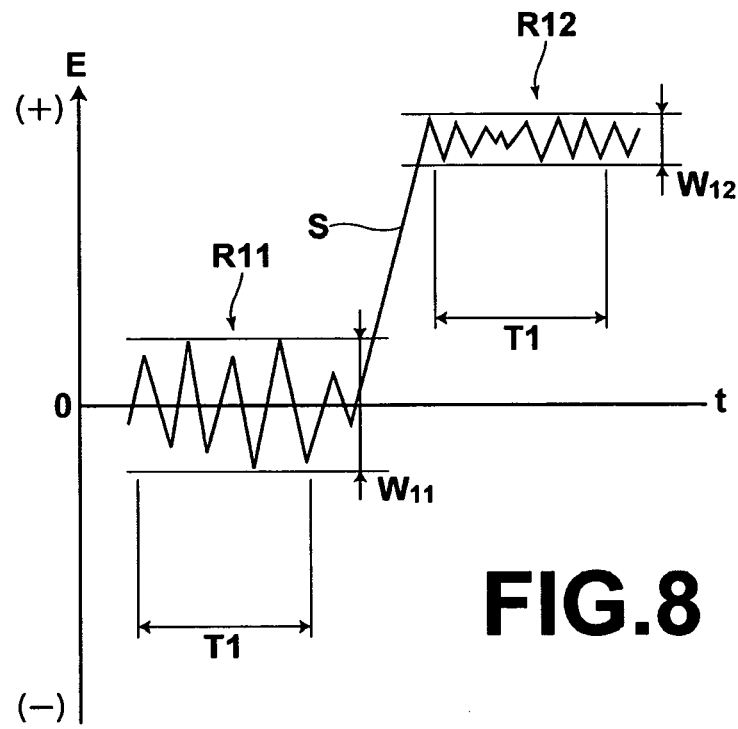
FIG. 8 is a graph that illustrates two types of fluctuations of signals, which are detected and output by the detecting section.
Figure 9:
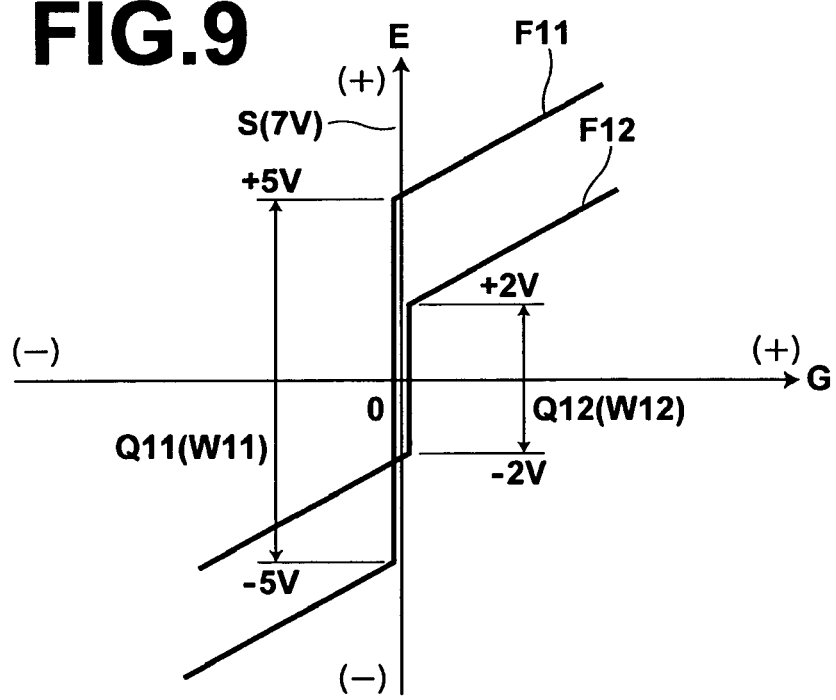
FIG. 9 is a graph that illustrates two types of control property curves that represent relationships between signal values that indicate external forces and movement assisting urging forces.

FIG. 8 is a graph having the values (voltages) of two types of signals S detected and output by the detecting section 30 plotted on a coordinate system having horizontal axis t that represents time and a vertical axis E that represents voltage. FIG. 9 is a graph that illustrates two types of control property curves that represent the relationships between voltages, which are the values of the signals S obtained by detecting external forces applied to the operating handle, and movement assisting urging forces which are generated by the movement assisting section 10 according to control by the control section, to which the voltages are input. The control property curves that represent the relationships between the voltages and urging forces are denoted by reference numerals F11 and F12. In addition, the dead zone ranges of the control property curves F11 and F12 are denoted by reference numerals Q11 and Q12, respectively.

Assume a case in which the judging section 50 judges that the operating handle 20 is not being operated when the fluctuating range W11 of voltages represented by the signals S is 10V or less over a predetermined amount of time T1, s illustrated in region R11 of FIG. 8. In this case, the control section 40 exhibits control properties F11 having a dead zone range of 10V (±5V), which is the same as this fluctuating range, as illustrated in FIG. 9.

Thereafter, the judging section 50 judges that the operating handle 20 is not being operated, because the fluctuating range W12 of voltages represented by the signals S is 4V or less over the predetermined amount of time T1.

In this case, the correcting section 60 may correct the control properties of the control section 40 to control properties F12 having a narrowed dead zone range of 4V (±2V), which is the same as the fluctuating range of voltage values of the non operative state signals S, as illustrated in FIG. 9.

That is, the correcting section 60 may correct the control properties (input properties) of the control section 40 such that the width of the dead zone range is increased when the fluctuating range of the values of the non operative state signals S increases, and the width of the dead zone range is decreased when the fluctuating range of the values of the non operative state signals S decreases.

Hereinafter, the operation of the radiation imaging apparatus 100 when changing the orientation of the radiation source 5 will be described.

Figure 10:
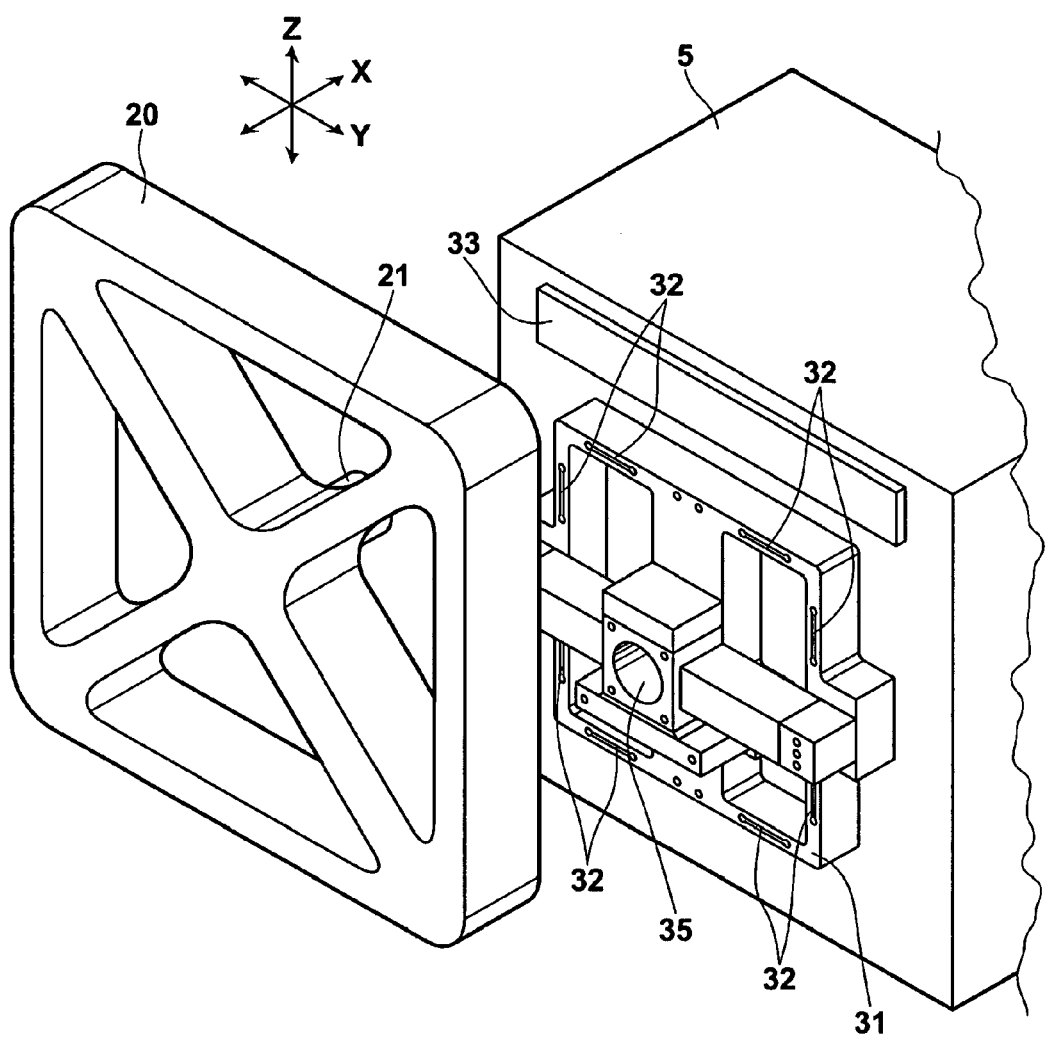
FIG. 10 is a magnified perspective view of an operating handle and a hardware portion of the detecting section.
Figure 11:
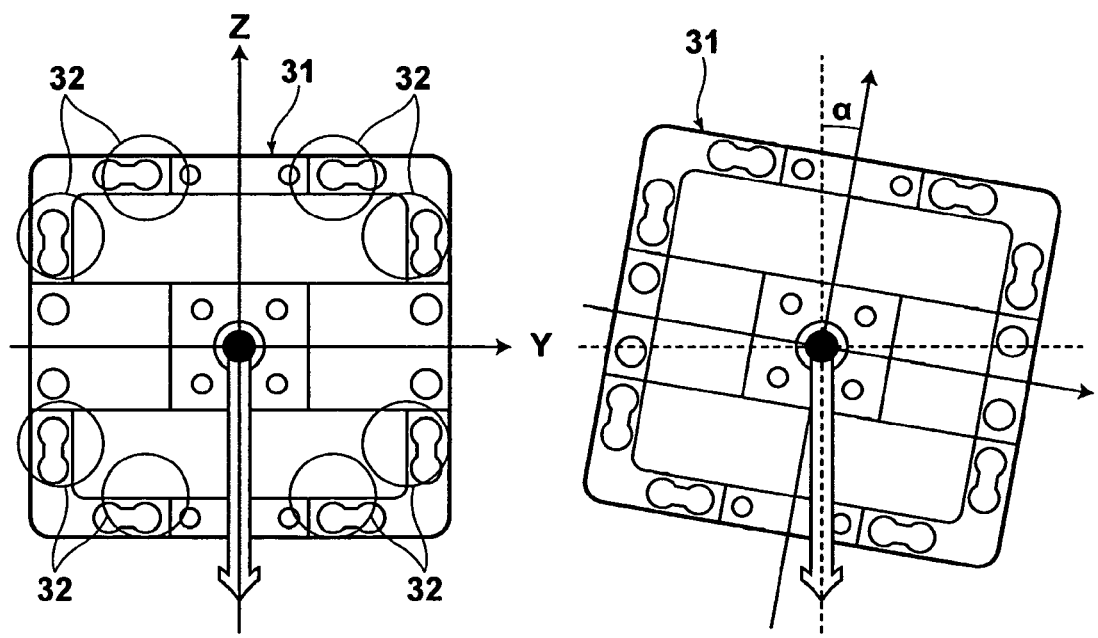
FIGS. 11A and 11B are diagrams that illustrate a standard state and an inclined state of the hardware portion.

FIG. 10 is a magnified perspective view of the operating handle 20 and a hardware portion 31 of the detecting section 30. FIGS. 11A and 11B are diagrams that comparatively illustrate a standard state and an inclined state of the hardware portion 31.

As illustrated in FIG. 10, the operating handle 20 is mounted to the radiation source 5 via the hardware portion 31 of the detecting section 30. That is, the hardware portion 31 is mounted on the radiation source 5, and the operating handle 20 is fixed to the hardware portion 31 by a shaft 21 that protrudes from the operating handle 20 engaging with the hardware portion 31 by way of the opening 35 provided in the hardware portion 31, to mount the operating handle 20 to the radiation source 5 via the hardware portion 31.

When external forces are applied to the operating handle 20, detecting regions 32 of the hardware portion 31, which have been processed to be easily strained, become strained. The strains of the detecting regions 32 are detected by strain gauges (not shown) which are mounted to each of the detecting regions 32. The outputs of the strain gauge of each of the detecting regions 32 are input to a circuit board 33, which is a software portion of the detecting section 30. The circuit board 33 receives input of the strain values detected by the strain gauges of the detecting regions 32, derives the intensity and direction of the external forces which are applied to the operating handle 20, and outputs these values as the signals S.

Here, when the orientation of the operating handle 20 changes, for example, due to a change in orientation of the radiation source 5, the force which is applied to each of the detecting regions 32 within the hardware portion 31 by the weight of the operating handle 20 itself changes. That is, when the hardware portion 31 is rotated for an angle α about the X axis from the standard state illustrated in FIG. 11A to the state illustrated in FIG. 11B, the amount of force which is applied to each of the detecting regions 32 changes, and the amount of strain generated at each of the detecting regions 32 changes as well. Here, a case in which the hardware portion 31 is rotated about the X axis will be described.

The output values of each of the strain gauges, which are input to the circuit board 33, change due to the change in strain generated at each of the detecting regions 32. For this reason, the values of the signals S that indicate the intensity and direction of external forces which are applied to the operating handle 20, derived from these output values, also change.

For example, in the case that the combined mass of the detecting section 30 and the operating handle 20 is 10 kg, and the change in orientation is an angle α ($α=1°$, the external force which is derived from the values output from the strain gauges change by approximately 1.7N (10 kg×sin α=approximately 0.17 kg, 0.17 kg×9.8 m/sec=approximately 1.7N).

In this case as well, correction that shifts the values of the non operative state signals S, which are detected by the detecting section 30 while external forces are not being applied to the operating handle, can be administered, such that the values of the non operative state signals S are included in the dead zone range with respect to control.

A strain gauge KFG-3-120-C1-23 by Kyowa was attached to a structural member molded from aluminum material with adhesive PC-6 and protected with Ak-22, to produce a force sensor similar to the detecting section 30. Repetitive external forces of ±approximately 100N (±approximately 10 kg·m/sec) were applied to the force sensor. As a result, it was confirmed that the values output from the force sensor when external forces are not being applied thereto changed approximately 5N (approximately 5 kg·m/sec) prior to and following application of the repetitive external forces.

Medical devices are commonly used for long periods of time, such as 10 years or longer. As described above, however, it is difficult to maintain the performance of force sensors in a constant state, and the costs incurred to do so are great. The present invention enables correction of the settings of dead zones to a correct state. Therefore, even if inexpensive sensors, of which the performance capabilities are likely to change, are employed, the dead zone range with respect to control of movement assistance can always be maintained in a correct and small range. As a result, favorable operability, in which the operating force required to initiate movement assistance is small, can be maintained.

Figure 12:
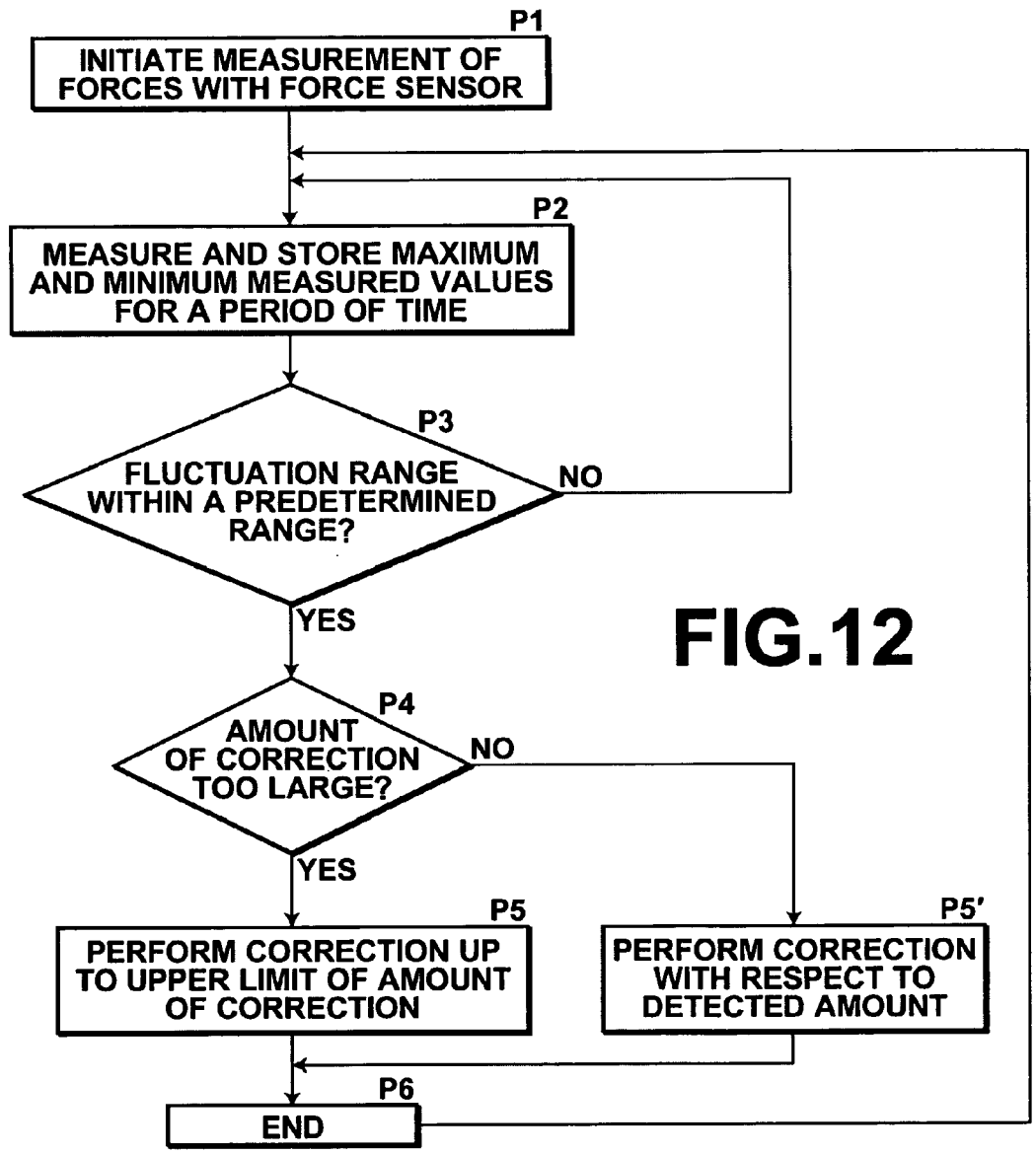
FIG. 12 is a flow chart that illustrates the steps of a correcting operation of the radiation imaging apparatus of the present invention.

FIG. 12 is a flow chart that illustrates the steps of the correcting operation of a radiation imaging apparatus of the present invention.

Hereinafter, operations which are somewhat different from those described with respect to the radiation imaging apparatus 100 will be described with reference to the flow chart of FIG. 12.

First, the operation starts at step P1, at which the detecting section 30 functions as a force sensor and initiates measurement of external forces applied to the operating handle 20.

Next, at step P2, the judging section 50 obtains the maximum value and the minimum value of the external forces measured by the detecting section over a predetermined amount of time.

Further, at step P3, the judging section 50 judges whether the difference between the measured maximum value and the measured minimum value of the external forces (the fluctuating range of the external forces) is within a predetermined range. In the case that it is judged that the fluctuation range of external forces is greater than the predetermined range, that is, when it is judged that external force is being applied to the operating handle 20, the process returns to step P2. On the other hand, in the case that the fluctuating range of the external forces is within the predetermined range, that is, when it is judged that external forces are not being applied to the operating handle 20, the process proceeds to step P4.

At step P4, it is determined whether the amount of correction required to cause the values of the non operative state signals S, which are output from the detecting section 30 while no external force is being applied to the operating handle 20, to correspond to the center of the dead zone range with respect to control is too great. In the case that the amount of correction required is too great, the process proceeds to step P5, and in the case that the amount of correction required is not too great, the process proceeds to step P5'.

At step P5, correction is performed up to an upper limit of the amount of correction, which is set in advance. That is, correction is administered such that the value of a signal corresponding to the center of the fluctuating range of the non operative state signals S, or the average value of the non operative state signals S corresponds to a position closer to the center of the dead zone range with respect to control. Thereafter, the process proceeds to step P6.

At step P5', correction is administered such that the value of a signal corresponding to the center of the fluctuating range of the signals S detected by the detecting section 30 while the operating handle 20 is not being operated, or the average value of the non operative state signals S corresponds to the center of the dead zone range with respect to control. That is, correction is performed such that the values of the non operative state signals S correspond to the center of the dead zone range with respect to control. Thereafter, the process proceeds to step P6.

Note that steps P5 and P5' are executed by the correcting section 60.

At step P6, the correcting operation ends.

Note that in the description above, cases in which movement of the radiation source is assisted have been described. However, the present invention is not limited to such a configuration, and may be applied to cases in which movement of the radiation detector or the like is assisted.

As described above, the present invention can automatically perform correction such that the signal values during non operative states are always within the dead zone range with respect to input signals for controlling power assistance, and more desirably, such that signal values correspond to the center of the dead zone range, even during radiation imaging.

For example, in the case that a signal detected by the detecting section is of a value that indicates that external force is being applied, even though external force is not being applied to the operating handle, the judging section can judge whether the signal is that which was detected during operation of the operating handle, regardless of the size of the signal value that represents the external force being applied to the operating handle. Accordingly, the values of such signals which are detected during non operative states can be corrected to be included in the dead zone range, or to correspond to the center of the dead zone range. Therefore, driving forces being generated by the movement assisting section even when no external force is being applied to the operating handle, resulting in the radiation source moving in an uncontrolled manner, can be prevented.

Further, by performing correction such that the average value and the like of the non operative state signals correspond to the center of the dead zone range with respect to control input, the driving force provided by the movement assisting section (assistance by the urging force) is initiated when the same amount of force is applied to the operating handle in either the forward and backward directions or the leftward and rightward directions. Therefore, the operability of movement assistance employing the operating handle can be improved.

Still further, even in cases that the setting of the dead zone with respect to control is shifted due to shocks imparted onto the apparatus, the power assistance urging force is generated when external force is not being applied to the operating handle, and the device moves in an uncontrollable manner, the judging section can judge whether external forces are being applied to the operating handle during the uncontrolled movement. Therefore, the correction described above can be performed, and the uncontrolled movement of the device can be ceased.

Further, the dead zone range can be enlarged or reduced corresponding to the fluctuating range of the non operative state signal values. Therefore, even in the case that the intensity of vibrations applied to the apparatus increases due to a change in the air conditioning system, for example, and as a result, the fluctuating range of the non operative state signals becomes greater than the dead zone range with respect to control, the correcting section can correct and enlarge the dead zone range such that the fluctuating range of the non operative state signals are included therein. Therefore, deterioration in operability of movement assistance employing the operating handle can be suppressed.

On the other hand, in the case that the fluctuating range of the non operative state signals is smaller than the dead zone range with respect to control, the correcting section can correct and reduce the dead zone range to correspond to the fluctuating range. Therefore, the urging force can be generated by application of smaller external forces, thereby improving the operability of movement assistance employing the operating handle.

Note that the above embodiment was described as a radiation imaging apparatus of the type which is suspended from the ceiling of a room. The present invention may also be applied to radiation imaging apparatuses of the floor based type, in which components move along rails provided on the floor of a room.

Figure 13:
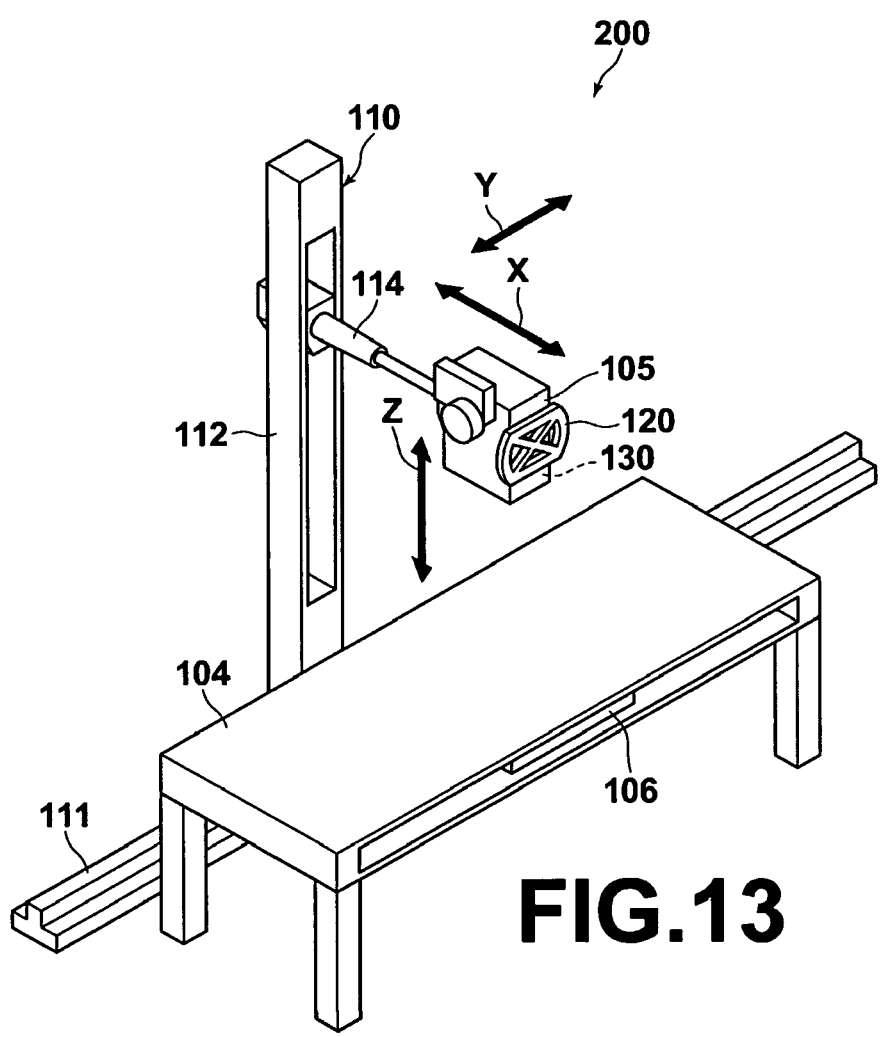
FIG. 13 is a diagram that illustrates an example of an upright radiation imaging apparatus to which the present invention is applied.

FIG. 13 is a diagram that illustrates a floor based radiation imaging apparatus 200, to which the present invention is applied. The floor based radiation imaging apparatus 200 is equipped with: a radiation source 105, which is a device to be employed in radiation imaging; an imaging table 104, on which a subject is supported in a supine position; a radiation detector 106, which is housed within the imaging table 104, for detecting radiation which is emitted from the radiation source 105 and passes through the subject; and a movement assisting section 110, for supporting and urging the radiation source 105 in the vertical direction and the horizontal direction, to assist manual movement thereof by an operator.

The floor based radiation imaging apparatus 200 is further equipped with: an operating handle 120, which is integrally formed with the radiation source 105, for operating the movement of the radiation source 105 that receives assistance from the movement assisting section 110; and a detecting section 130, for detecting external forces which are applied to the operating handle 120 and outputs signals S that indicate the intensity and direction of the external forces.

The movement assisting section 110 urges the radiation source 105 to reduce the amount of necessary external force which is applied to the operating handle 120 by the operator when moving the radiation source 105. That is, the movement assisting section 110 assists movement of the radiation source 105 by the operator.

The movement assisting section 110 is equipped with fixed rails 111 which are provided on the floor surface; a movable column 112 which is capable of moving in the direction that the fixed rails 111 extend in (the direction indicated by arrow Y in FIG. 13) while engaged with the fixed rails 111; a horizontal telescoping arm 114, which is movable in the vertical direction that the movable column 112 extends in (the direction indicated by arrow Z in FIG. 13) and also capable of extending and contracting in the horizontal direction (the direction indicated by arrow X in FIG. 13) by telescopic motion; and drive motors (not shown) for moving the movable column 112 in the Y direction, for moving the horizontal telescoping arm 114 in the Z direction, and for extending and contracting the horizontal telescoping arm 114 in the X direction.

Note that in addition to the fixed rails 111 which are provided on the floor surface, additional rails may be provided on a wall surface or on the ceiling. By causing these additional fixed rails to engage with the movable column 112, unnecessary positional displacement of the movable column 112 in directions other than the Y direction can be reduced.

The radiation source 105 is mounted to the end of the horizontal telescoping arm 114. The radiation source 105 is capable of changing its orientation with respect to the horizontal telescoping arm 114.

Here, the operating handle 120 is integrally mounted onto the radiation source 105 via the detecting section 130. The detecting section 130 detects the intensity and direction of external forces which are applied to the operating handle 120.

The other components and operations of the floor based radiation imaging apparatus 200 are the same as those of the suspended type radiation imaging apparatus 100 which was described with reference to FIG. 1 and FIG. 2.

Figure 14:
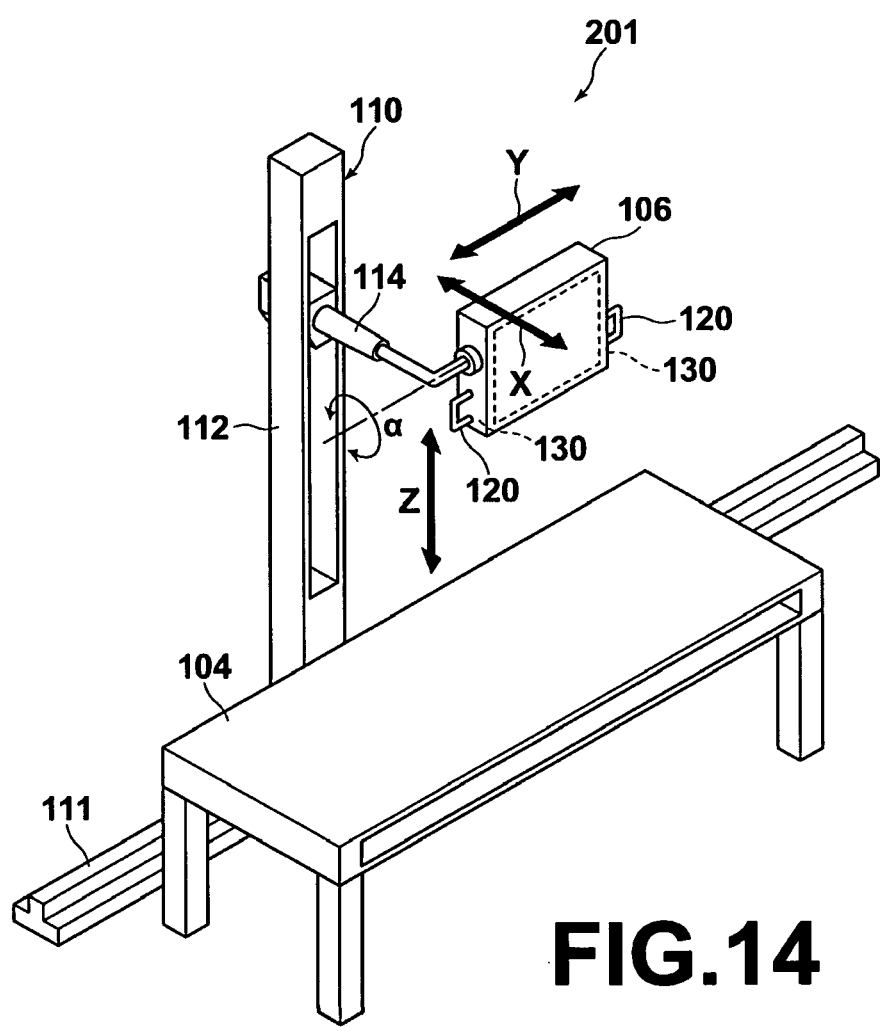
FIG. 14 is a diagram that illustrates another example of an upright radiation imaging apparatus to which the present invention is applied.

The radiation imaging apparatus 200 described above with reference to FIG. 13 is of the type in which the radiation source is movable in the X, Y, and Z directions. However, the present invention may also be applied to a floor based radiation imaging apparatus having a radiation detector mounted on an operating block. FIG. 14 illustrates a radiation imaging apparatus 201 of this type. Note that in FIG. 14, structural elements which are the same as those illustrated in FIG. 13 are denoted with the same reference numerals, and descriptions thereof will be omitted insofar as they are not particularly necessary.

The radiation imaging apparatus 201 of FIG. 14 has a radiation detector 106 mounted on the end of the horizontal telescoping arm 114 instead of the radiation source 105.

The radiation detector 106 is capable of rotating about an axis that extends in the horizontal direction in the directions indicated by arrow $\alpha$ either by manual operation or by a driving means. In addition, operating handles 120, for moving the radiation detector 106 in the X, Y, and Z directions and for rotating the radiation detector 106 in the $\alpha$ directions, are fixed on the side surfaces of the radiation detector 106.

The radiation imaging apparatus 201 is capable of moving the radiation detector 106 to a position removed from the imaging table 104 for supine imaging (for example, a position toward the upper right of FIG. 14). The radiation detector 106 may be set to the orientation illustrated in FIG. 14 such that the detecting surface thereof is perpendicular to the floor surface at this removed position. Then, a radiation source (not shown) which is suspended from the ceiling and is freely movable, for example, may be employed to perform radiation imaging of a subject in an upright state.

In addition, the radiation detector 106 may be moved to a position toward the side of the imaging table 104 for supine imaging, and rotated 90° in the direction a from the orientation illustrated in FIG. 14 such that the detecting surface thereof faces upward and is parallel to the floor surface. Thereafter, the radiation detector 106 may be lowered, then the horizontal telescoping arm 114 may be extended, to position the radiation detector 106 beneath the imaging table 104 for supine imaging. In this state, radiation may be emitted toward a subject in a supine position on the imaging table 104 from the radiation source, and the radiation detector 106 may detect the radiation which passes through the subject, to perform radiation imaging of the subject in the supine position.

In addition to the fixed rails 111 which are provided on the floor surface, additional rails may be provided on a wall surface or on the ceiling in the radiation imaging apparatus 201, in the same manner as in the apparatus of FIG. 13. By causing these additional fixed rails to engage with the movable column 112, unnecessary positional displacement of the movable column 112 in directions other than the Y direction can be reduced.

What is claimed is:

1. A radiation imaging apparatus, comprising:
    movement assisting means, for assisting manual movement of a device which is employed to perform radiation imaging, by urging the device;
    an operating portion that enables operation of a movement of the device, which is assisted by the movement assisting means;
    detecting means, for detecting external forces which are applied to the operating portion, and outputs signals indicating intensities and directions of the external forces;
    control means, for controlling the movement assisting means to assist movement of the device in the directions of the external forces indicated by the signals output from the detecting means, and for controlling the movement assisting means to not assist manual movement of the device when the values of the signals are included within a dead zone range;
    judging means, for judging whether the operating portion is being operated based on a state of change of the signals regardless of the intensities of the values of the signals; and
    correcting means, for performing corrections such that the values of signals, which are obtained while it is judged that the operating portion is not being operated, are included in the dead zone range with respect to control exerted by the control means.

2. A radiation imaging apparatus as defined in claim 1, wherein:
the judging means judges that the operating portion is not being operated when the values of signals which are output from the detecting means are constant.

3. A radiation imaging apparatus as defined in claim 2, wherein:
the correcting means performs corrections such that a signal value corresponding to the center of a fluctuating range of the signals, which are output from the detecting means while it is judged that the operating portion is not being operated, corresponds to the center of the dead zone range with respect to control exerted by the control means.

4. A radiation imaging apparatus as defined in claim 2, wherein:
the correcting means changes a width of the dead zone range according to a fluctuation range of the signals, which are output from the detecting means while it is judged that the operating portion is not being operated.

5. A radiation imaging apparatus as defined in claim 1, wherein:
the judging means judges that the operating portion is not being operated when a fluctuating range of the signals which are output from the detecting means is a predetermined range or less, and judges that the operating portion is being operated when the fluctuating range of the signals which are output from the detecting means is greater than the predetermined range.

6. A radiation imaging apparatus as defined in claim 5, wherein:
the correcting means performs corrections such that a signal value corresponding to the center of the fluctuating range of the signals, which are output from the detecting means while it is judged that the operating portion is not being operated, corresponds to the center of the dead zone range with respect to control exerted by the control means.

7. A radiation imaging apparatus as defined in claim 5, wherein:
the correcting means changes a width of the dead zone range according to the fluctuation range of the signals, which are output from the detecting means while it is judged that the operating portion is not being operated.

8. A radiation imaging apparatus as defined in claim 1, wherein:
the judging means judges that the operating portion is not being operated when a fluctuation of the signals which are output from the detecting means are repetitions of a same fluctuation pattern, and judges that the operating portion is being operated when the fluctuation of the signals which are output from the detecting means are not repetitions of the same fluctuation pattern.

9. A radiation imaging apparatus as defined in claim 8, wherein:
the correcting means performs corrections such that a signal value corresponding to the center of a fluctuating range of the signals, which are output from the detecting means while it is judged that the operating portion is not being operated, corresponds to the center of the dead zone range with respect to control exerted by the control means.

10. A radiation imaging apparatus as defined in claim 8, wherein:
the correcting means changes a width of the dead zone range according to a fluctuation range of the signals, which are output from the detecting means while it is judged that the operating portion is not being operated.

11. A radiation imaging apparatus as defined in claim 1, wherein:
the correcting means performs corrections such that a signal value corresponding to the center of a fluctuating range of the signals, which are output from the detecting means while it is judged that the operating portion is not being operated, corresponds to the center of the dead zone range with respect to control exerted by the control means.

12. A radiation imaging apparatus as defined in claim 1, wherein:
the correcting means performs corrections such that an average value of the signals, which are output from the detecting means while it is judged that the operating portion is not being operated, corresponds to the center of the dead zone range with respect to control exerted by the control means.

13. A radiation imaging apparatus as defined in claim 1, wherein:
the correcting means changes a width of the dead zone range according to a fluctuation range of the signals, which are output from the detecting means while it is judged that the operating portion is not being operated.

14. A radiation imaging apparatus as defined in claim 1, wherein:
the correcting means administers correction on at least one of the signals which are output from the detecting means and control properties of the control means.

15. A radiation imaging apparatus as defined hi claim 1, wherein:
the movement assisting means assists movement of the device in vertical and horizontal directions, while supporting the device in a state in which the device is suspended from the ceiling of a room.

16. A radiation imaging apparatus as defined in claim 1, wherein:
the device is capable of changing its orientation with respect to the movement assisting means.

17. A radiation imaging apparatus as defined in claim 1, wherein:
the device is one of a radiation source to be employed in radiation imaging and a radiation detector to be employed in radiation imaging.

* * * * *